(12) United States Patent
Qian

(10) Patent No.: US 9,802,934 B2
(45) Date of Patent: Oct. 31, 2017

(54) PROCESS FOR THE SYNTHESIS OF (R)-PRAZIQUANTEL

(71) Applicant: TONGLI BIOMEDICAL CO., LTD., Zhangjigang, Jiangsu (CN)

(72) Inventor: Mingxin Qian, Jiangsu (CN)

(73) Assignee: TONGLI BIOMEDICAL CO., LTD., Zhangjigang (CN)

( * ) Notice: Subject to any disclaimer, the term of this patent is extended or adjusted under 35 U.S.C. 154(b) by 0 days.

(21) Appl. No.: 15/403,898

(22) Filed: Jan. 11, 2017

(65) Prior Publication Data

US 2017/0121330 A1    May 4, 2017

Related U.S. Application Data

(63) Continuation-in-part of application No. 15/029,991, filed as application No. PCT/CN2014/088700 on Oct. 16, 2014, now Pat. No. 9,657,017.

(30) Foreign Application Priority Data

Oct. 17, 2013  (CN) .......................... 2013 1 0488773

(51) Int. Cl.
  *C07D 487/14*  (2006.01)
  *C07D 471/04*  (2006.01)
  *C07D 217/26*  (2006.01)
(52) U.S. Cl.
  CPC ......... *C07D 471/04* (2013.01); *C07D 217/26* (2013.01); *C07B 2200/13* (2013.01)

(58) Field of Classification Search
  CPC .................................................... C07D 487/14
  USPC ........................................................ 544/344
  See application file for complete search history.

(56) References Cited

FOREIGN PATENT DOCUMENTS

| CN | 102911979 A | 2/2013 |
|---|---|---|
| CN | 103160562 | 6/2013 |
| CN | 103333931 A | 10/2013 |

*Primary Examiner* — Douglas M Willis
(74) *Attorney, Agent, or Firm* — Baker, Donelson, Bearman, Caldwell & Berkowitz, PC; Cong Ding

(57) ABSTRACT

The present disclosure relates to a process and new intermediates for the synthesis of (R)-praziquantel, which is obtained through four steps in proper order, that is, condensation reaction, reduction reaction, acylation reaction and ring-closing reaction, using (1R)-2-substituted-1,2,3,4-tetrahydroisoquinoline-1-carboxylic acid as starting material. Overall, the present disclosure provides a (R)-praziquantel product with higher optical purity through a process route that is more cost effective and environmentally friendly.

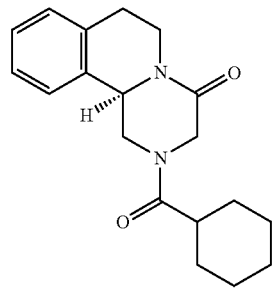

(R)-praziquantel

11 Claims, 1 Drawing Sheet

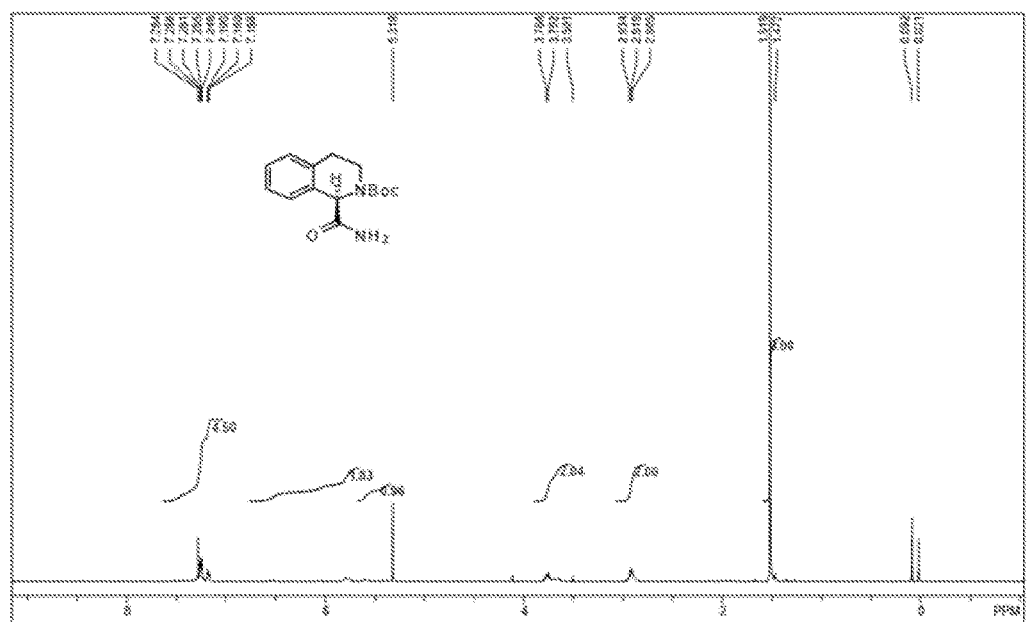

PROCESS FOR THE SYNTHESIS OF (R)-PRAZIQUANTEL

CROSS REFERENCE TO RELATED APPLICATIONS

The present application is a continuation-in-part application of U.S. patent application Ser. No. 15/029,991 filed on Apr. 15, 2016, which is a §371 National State Application of PCT/CN2014/088700 filed Oct. 15, 2014 which claims priority to CN 201310488773.4 filed Oct. 17, 2013, the entire disclosure of which are hereby incorporated by reference in their entirety.

TECHNICAL FIELD OF THE INVENTION

The present disclosure relates to a process and intermediates for the synthesis of (R)-praziquantel, and a pharmaceutical composition comprising (R)-praziquantel thus prepared.

BACKGROUND OF THE INVENTION

Praziquantel is a synthesized pyrazine isoquinoline derivative, also called cyclo-praziquantel, and is a white or off-white crystalline powder and bitter in taste. It is worldwide recognized as a highly effective and broad-spectrum anti-parasitic drug, and is widely used for treating diseases such as schistosomiasis *japonica*, schistosomiasis *haematobium*, schistosomiasis *mansoni*, clonorchiasis, paragonimiasis, sparganosis *mansoni, fasciolopsis*, echinococcosis, taeniasis, cysticercosis, etc. It has advantages such as broad spectrum, high efficacy, low toxicity, short therapeutic course and easy to use, etc. In addition to human use, it is also widely used as an anti-parasitic treatment in animals including poultry and livestock. The invention of praziquantel is a major breakthrough in the history of anti-parasitic chemotherapy. In the past 30 years, praziquantel has been the choice of drug for treating various parasitic diseases on the market.

Praziquantel is a racemic mixture composed of (R)-praziquantel and (S)-praziquantel. Scientists have separated and obtained both pure optic isomers of (R)-praziquantel and (S)-praziquantel from synthesized praziquantel, and found in preclinical studies and preliminary clinical trials that: (R)-praziquantel is the active parasiticidal component of praziquantel, while the (S)-praziquantel is inactive or even harmful; at the same dosage, the clinical efficacy of (R)-praziquantel is better than that of praziquantel, where (S)-praziquantel is almost inactive, bitter taste and the major source of side effects. (R)-praziquantel shows lower cardiac toxicity than (S)-praziquantel. Therefore, the development of (R)-praziquantel has substantial clinical values of higher efficacy, less side effects, and better medical compliance, and is highly expected by the World Health Organization for global anti-parasitic chemotherapy. However, the difficult technical problem of low synthetic yield of (R)-praziquantel has been unsolved for many years.

Praziquantel was firstly synthesized in 1975 by Seubert et al, and two pharmaceutical companies in Germany, E. Merck and Bayer AG, have successfully developed this drug, which was the first to appear in the market in the trade name of Cesol in 1980 and now is widely used around the world. The manufacture process of praziquantel has used some toxic and harmful chemicals, such as potassium cyanide, heavy metals, etc., and it has a lengthy route, and rigorous reaction conditions such as high temperature, high pressure. Also, this type of reaction process is difficult to control, and may cause severe pollution.

At present, there are two main approaches for the synthesis of (R)-praziquantel:

1. Chemical resolution: using racemic intermediates or racemic praziquantel as raw material, (R)-praziquantel is synthesized through chemical resolution (Resolution of Praziquantel, Matthew H. Toddl, Australia, PLOS, Neglected Tropical Diseases, September 2011, Volume 5, Issue 9, e1260). In addition to the potential environmental disadvantages of the synthesis of praziquantel, the yield and optical purity of obtained (R)-praziquantel require to be improved, and (S)-praziquantel amine after resolution needs to be recycled and racemized for reuse, which consumes more energy and time.

2. Enzymatic resolution as reported in CN 102911979 A: it needs to racemize dextroisomer, and has a cumbersome process and an overall yield to be improved.

SUMMARY OF THE INVENTION

One objective of the present disclosure is to provide a new process for the synthesis of (R)-praziquantel.

To achieve the above purpose, the present disclosure provides a process for the synthesis of (R)-praziquantel, which employs the following synthesis route:

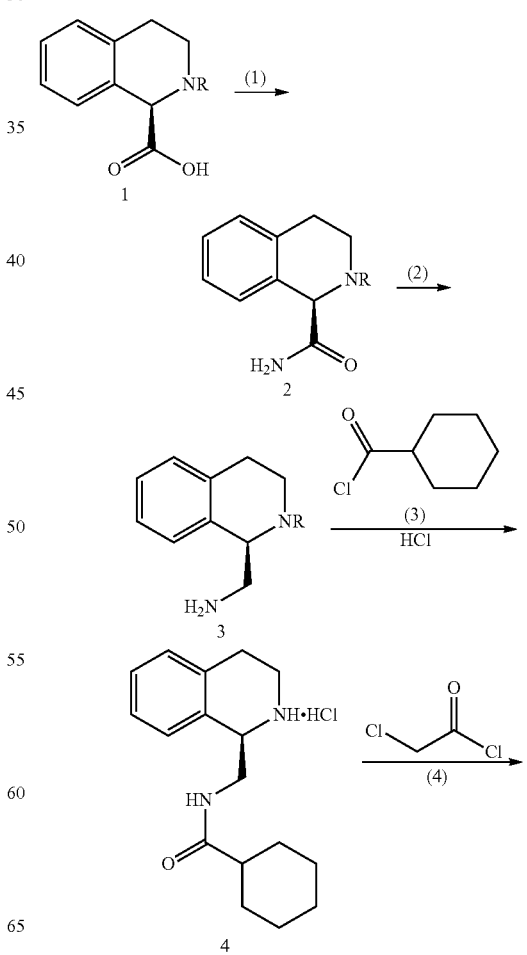

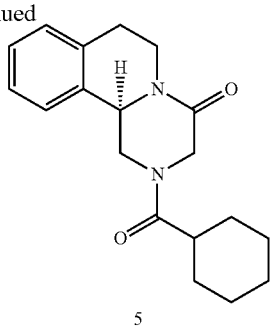

in the above formula, R is an amino protective group and HCl may be substituted by other acids.

The above-mentioned route comprises four steps, steps (1)-(4). In step (1), compound 1 is reacted through a condensation-acylation reaction to obtain compound 2. In step (2), compound 2 is reacted through a reduction reaction to obtain compound 3. In step (3), compound 3 is reacted with cyclohexyl formyl chloride and de-protective agent such as hydrochloric acid and other acids to obtain compound 4. In step (4), compound 4 is reacted with chloroacetyl chloride through ring-closing reaction to obtain compound 5.

Chemical name of compound 1-5 are listed below:
Compound 1:
(1R)-2-[(tert-butyl) oxycarbonyl]-1,2,3,4-tetrahydroisoquinoline-1-carboxylic acid.
Compound 2:
(1R)-2-[(tert-butyl)oxycarbonyl]-1,2,3,4-tetrahydroisoquinoline carboxylic amide
Compound 3:
(1R)-2-[(tert-butyl) oxycarbonyl]-1,2,3,4-tetrahydroisoquinoline carboxylic amine.
Compound 4:
N—(((R)-1,2,3,4-tetrahydroisoquinoline-1-yl)methyl) cyclohexanecarboxamide hydrochloride
Compound 5:
(1R)-2-(cyclohexanecarbonyl)-3,6,7,11b-tetrahydro-1H-pyrazino[2,1-a]isoquinolin-4-one.

According to the present invention, the above-mentioned R includes, but not limited to, tert-butyloxycarbonyl, benzyloxycarbonyl, fluorenylmethoxycarbonyl, allyloxycarbonyl, trichloroethoxycarbonyl, p-methoxybenzyl, and benzyl, etc.

According to the present disclosure, in the step (1), the reaction converting compound 1 into compound 2 is a condensation-acylation reaction of a carboxylic acid and ammonia, which may employ a direct method, a mixed acid anhydride method, or a condensation agent method, wherein the mixed acid anhydride method is preferred.

According to one aspect of the present disclosure, in the step (1), compound 1 is reacted with chloro-carbonic ester (for example, methyl chloroformate, ethyl chloroformate, and isobutyl chloroformate) to get an active ester in the present of alkali and in a solvent, and then reacted with ammonia gas.

According to another aspect of the present disclosure, in the step (1), compound 1 may also be reacted with ammonia in the presence of N, N'-carbonyldiimidazole (CDI) to obtain compound 2.

According to a preferred aspect of the present disclosure, in the step (2), a system of sodium borohydride/trifluoroboric acid/ether is employed to reduce compound 2.

According to a preferred aspect of the present disclosure, the reaction in the step (3) is conducted in the presence of an alkali and in a solvent, wherein the alkali is preferably pyridine, and the solvent is preferably dichloromethane.

According to a specific aspect of the present disclosure, the step (3) comprises adding compound 3 and pyridine into acetonitrile, cooling to about 0° C. to about 5° C., slowly dropwise adding a solution of cyclohexyl formyl chloride dissolved in dichloromethane, then stirring at room temperature after the addition being over, conducting routine post-treatment to obtain an intermediate product, and further reacting the said intermediate product with HCl saturated ethyl acetate solution for removal of protective group.

According to another preferred aspect of the present disclosure, the reaction in the step (4) is conducted in the presence of an alkali and in a solvent, wherein the alkali is preferably sodium hydroxide, potassium hydroxide, potassium tert-butoxide and organic amine, etc., and the solvent is preferably dichloromethane.

Further preferably, the reaction of the step (4) is conducted in the presence of phase transfer catalyst, which may be a quaternary ammonium salt phase transfer catalyst, specifically such as benzyltriethylammonium chloride.

Preferably, the present disclosure further includes a step of preparing compound 1 which comprises oxidizing compound of formula a and/or compound of formula b

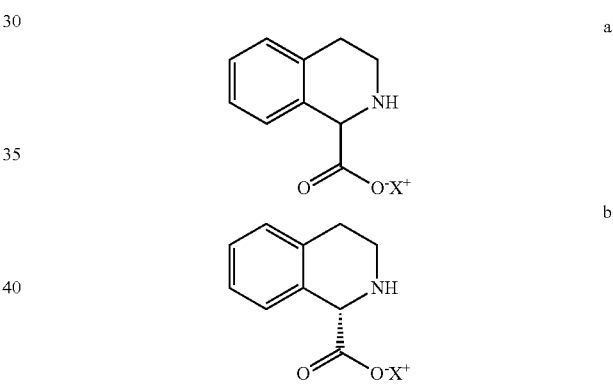

in the presence of recombinant D-amino acid oxidase, catalase and oxygen to give an oxidation product, and reducing the oxidation product by borane-amino complex to form an intermediate of formula c,

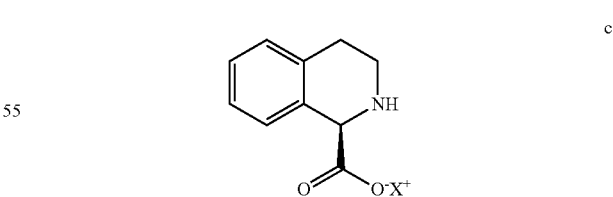

and further synthesizing compound 1 from the intermediate of formula c, the $X^+$ in formula a, b and c are the same and represent an anion portion that is counter to carboxylate ion.

The second objective of the present disclosure is to provide an intermediate for the synthesis of (R)-praziquantel having a structure as shown in formula 2:

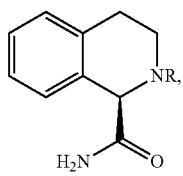

in formula 2, R is an amino protective group.

In formula 2, R specifically is tert-butyloxycarbonyl (Boc), benzyloxycarbonyl, fluorenylmethoxycarbonyl, allyloxycarbonyl, trichloroethoxycarbonyl, p-methoxybenzyl or benzyl, etc., wherein tert-butyloxycarbonyl is preferred.

The third object of the present disclosure is to provide a crystalline form and/or an amorphous form of (R)-praziquantel prepared by the process according to the invention.

The forth object of the present invention is to provide a pharmaceutical composition comprising an active ingredient comprising the crystalline form and/or the amorphous form of (R)-praziquantel prepared by the process according to the invention, and a pharmaceutically acceptable carrier Preferably, the pharmaceutical composition is used for preventing and/or treating parasitic diseases.

Preferably, the crystalline form of (R)-praziquantel having the X-ray diffraction pattern (CuKα radiation) of the crystal format 25° C. which shows the following seven diffraction peaks: 2-Theta=6.9±0.2°, 8.3±0.2°, 15.1±0.2°, 17.4±0.2°, 19.8±0.2°, 21.9±0.2°, 24.3±0.2° or d=12.74±0.20 Å, 10.61±0.20 Å, 5.87±0.20 Å, 5.09±0.20 Å, 4.48±0.20 Å, 4.06±0.20 Å, 3.66±0.20 Å.

Further, the X-ray diffraction pattern (CuKα radiation) of the crystal form at 25° C. further shows the following fifteen diffraction peaks: 2-Theta=13.4±0.2°, 14.1±0.2°, 15.7±0.2°, 16.6±0.2°, 17.9±0.2°, 18.2±0.2°, 19.0±0.2°, 20.6±0.2°, 23.8±0.2°, 27.4±0.2°, 28.5±0.2°, 29.0±0.2°, 30.9±0.2°, 33.7±0.2°, 39.5±0.2° or d=6.59±0.20 Å, 6.29±0.20 Å, 5.63±0.20 Å, 5.33±0.20 Å, 4.96±0.20 Å, 4.86±0.20 Å, 4.68±0.20 Å, 4.31±0.20 Å, 3.74±0.20 Å, 3.25±0.20 Å, 3.13±0.20 Å, 3.07±0.20 Å, 2.89±0.20 Å, 2.66±0.20 Å, 2.28±0.20 Å.

Further, the X-ray diffraction pattern (CuKα radiation) of the crystal format at 25° C. further shows the following five diffraction peaks: 2-Theta=8.67±0.2°, 23.0±0.2°, 25.4±0.2°, 27.8±0.2°, 32.4±0.2° or d=10.19±0.20 Å, 3.86±0.20 Å, 3.50±0.20 Å, 3.20±0.20 Å, 2.76±0.20 Å.

Due to the implementations of the above technical solutions, the present disclosure has the following advantages over the prior art: the present disclosure provides a new synthetic route of (R)-praziquantel, and respective steps of which is consisted all are common reactions having mature conditions and simple operation. Overall, the present disclosure may obtain a (R)-praziquantel product with a higher optical purity and yield, through a more cost effective and environmentally friendly process.

BRIEF DESCRIPTION OF THE DRAWINGS

FIG. 1 depicts the NMR spectrum of compound 2A prepared in example 11.

DETAILED DESCRIPTION OF EXEMPLARY EMBODIMENTS

The synthetic route of (R)-praziquantel is as follow:

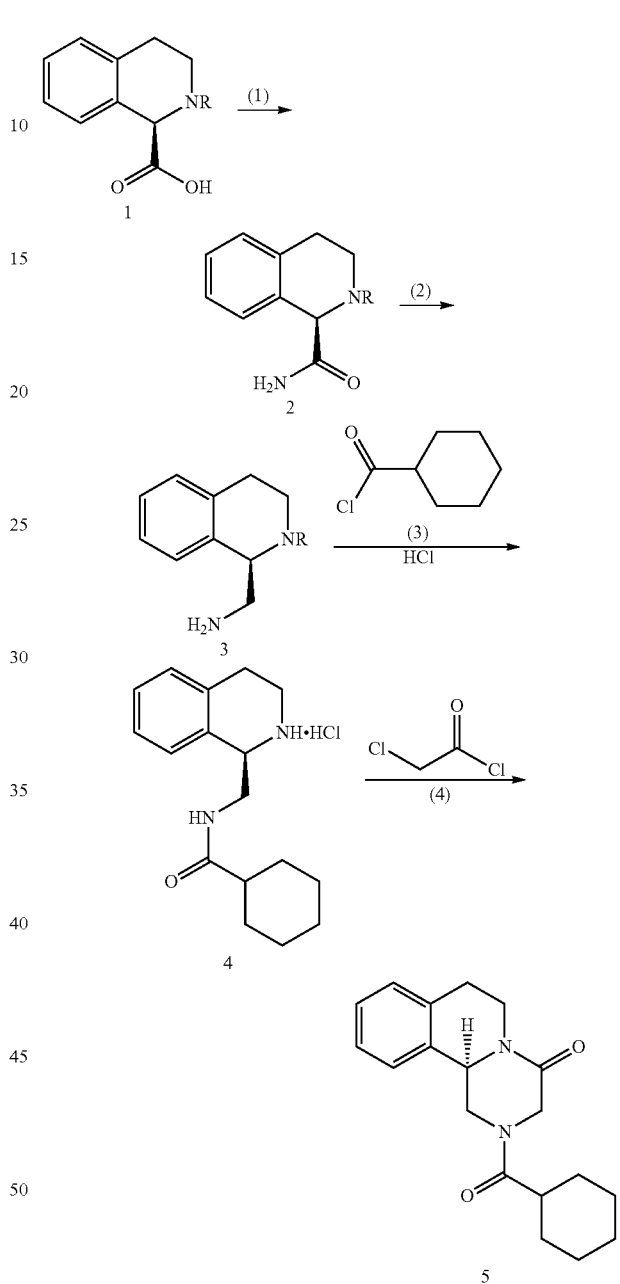

in the above formula, R is an amino protective group and HCl may be substituted by other acid for removal of protective group. The amino protective group may be a common one, specifically such as tert-butyloxycarbonyl (Boc).

In the above route, the major key point is to obtain compound 3 through two step of reactions in steps (1) and (2) using compound 1 as starting material, wherein compound 2 is a new intermediate for the synthesis of (R)-praziquantel. The process using compound 2 as the intermediate achieves a higher yield, lower cost and is easier to operate.

According to one aspect of the present disclosure, in the step (1), firstly compound 1 is reacted with chloro-carbonic ester (for example, methyl chloroformate, ethyl chloroformate, and isobutyl chloroformate) in the presence of an alkaline substance such as pyridine and in a solvent, precipitates are filtered out after the reaction ends, and ammonia gas is led into the reaction liquid to form compound 2. The solvent may be, for example, tetrahydrofuran. Further, step (1) may be specifically implemented as follow: adding compound 1 into tetrahydrofuran and cooling to about 0° C. to about 5° C., adding pyridine, dropwise adding chloroformate (for example, methyl chloroformate, ethyl chloroformate, and isobutyl chloroformate), filtering out precipitate, stirring filtered liquid for about 1 hour to about 1.5 hours, leading in ammonia gas, stirring overnight at room temperature, adding water, extracting by ethyl acetate, drying over anhydrous sodium sulfate, filtering, concentrating, mashing the residual with petroleum ether to give compound 2.

According to the present disclosure, in the step (1), compound 1 may also be reacted with ammonia in the presence of N, N'-carbonyldiimidazole (CDI) to obtain compound 2. According to one aspect of the present invention, compound 1 is firstly reacted with N, N'-carbonyldiimidazole in a solvent to obtain a carbonyl imidazole intermediate, and then the carbonyl imidazole intermediate is reacted with ammonia to form compound 2. Further, step (1) may be implemented as follow: compound 1 is dissolved into a solvent, added with N, N'-carbonyldiimidazole, stirred at room temperature for more than about 5 minutes, then cooled down to below about 10° C., and dropwise added with aqueous ammonia to react. Wherein, stirring time at room temperature is preferably about 10 minutes to about 30 minutes, and when dropwise adding aqueous ammonia, the reaction system is preferably controlled to a temperature of about 0° C. to about 5° C. The solvent is preferably tetrahydrofuran. Preferably, the crude product is purified by silica gel column chromatography with an eluent of methyl alcohol: dichloromethane is about 0:100 to about 5:95. Preferably, the eluent consists of dichloromethane and methyl alcohol of a volume ratio of about 15:1 to about 25:1.

In the step (2), a system of sodium borohydride/trifluoro boric acid/ether is employed to reduce compound 2.

According to a specific aspect, the step (2) is specifically implemented as follow: compound 2 is added into tetrahydrofuran, then at room temperature and under argon protection, the reaction system is batchwise added with sodium borohydride, heated to reflux, dropwise added with boron trifluoride diethyl etherate, stirred the generated suspension liquid for about 1.5 hours to about 3 hours, and the reaction is ended after detecting disappearance of compound 2 by TLC test when gas releasing is not obvious. The reaction liquid is poured into HCl in ice water, adjusted pH to about pH 8.5 to about pH 9.5, extracted with dichloromethane for three times, washed by saturated NaCl solution, dried by anhydrous sodium sulfate, and filtered to remove solvents to give a crude product, i.e. compound 3, which is directly used in the next step.

According to another specific aspect, the step (2) is specifically implemented as follow: compound 2 is dissolved into a solvent, added with sodium borohydride under nitrogen protection and an ice bath, dropwise added with boron trifluoride diethyl etherate while keeping the temperature below about 10° C., and after addition, stirred to react at about 20° C. to about 25° C., wherein the solvent is preferably tetrahydrofuran, and the stirring time is preferably about 30 hours to about 42 hours. Preferably, the temperature is cooled down to about 0° C. to about 5° C., and water is dropwise added to quench the reaction. Preferably, the obtained crude product is purified by column chromatography with a mixed solvent of dichloromethane and methanol of a volume ratio of about 19:1.

According to a preferred aspect of the present disclosure, the reaction in the step (3) is conducted in the presence of alkali and in a solvent, wherein the alkali is preferably pyridine, and the solvent is preferably acetonitrile. A specific implementation is as follow: compound 3 is added into acetonitrile, added with pyridine, cooled down to about 0° C. to about 5° C., slowly dropwise added with a solution of cyclohexyl formyl chloride dissolved in dichloromethane, and after addition, stirred to react at room temperature. After routine post-treatment, the de-protected product is obtained by reacting with hydrochloric acid saturated ethyl acetate solution.

According to another preferred aspect of the present disclosure, the reaction in step (4) is conducted in the presence of alkali and in a solvent, wherein the alkali is preferably sodium hydroxide, potassium hydroxide, potassium tert-butoxide and organic amine, etc., and the solvent is preferably dichloromethane. As a preferred scheme, the reaction of step (4) is conducted in the presence of phase transfer catalyst, the said phase transfer catalyst may employ a quaternary ammonium salt, specifically such as benzyltriethylammonium chloride.

In a specific implementation, the step (3) is implemented as follow: a solution of compound 4 in dichloromethane is added into a solution of chloroacetyl chloride in dichloromethane, then added with one or more selected from a group consisting of sodium hydroxide, potassium hydroxide, potassium tert-butoxide and organic amine, stirred for about 20 minutes to about 40 minutes, added with benzyltriethylammonium chloride, and heated to reflux until the reaction finishes. Wherein, sodium hydroxide, potassium hydroxide, potassium tert-butoxide or organic amine may be added as their original forms, and may also be added after being prepared to an aqueous solution, and the latter one is preferred. According to a specific aspect, it is preferable to add an aqueous solution of sodium hydroxide of about 30 wt % to about 50 wt %.

The present disclosure further provides a process of preparing compound 1 which utilizes recombinant D-amino acid oxidase and water-soluble borane-amino complex to high effectively in situ deracemize and prepare (R)-1,2,3,4-tetrahydroisoquinoline-1-carboxylic acid and then obtain compound 1. Employing the method according to the present disclosure, only a small amount of enzyme catalyst is required, the post treatment is very simple, and also the harm and pollution of traditional chemical method for preparing praziquantel and its intermediates are avoided. Compared with the traditional chemical method, advantages of the method are that: avoiding the use of highly toxic raw materials such as sodium cyanide and heavy metals, avoiding high temperature and high pressure and other dangerous reactions, reducing the amount of organic solvents and reduce environmental pollution from the production of praziquantel and its intermediates; solving problems in early biological method of preparing praziquantel and its intermediates such as large amount of enzyme, low substrate concentration, complicated post-treatment, high energy consumption, low efficiency, difficulty to control, etc.

Further, the borane-amine complex is one or more selected from a group consisting of borane-ammonia complex, borane-dimethylamine complex, borane-triethylamine complex, borane-tert-butylamine complex, borane-diethylamine complex, and borane-N, N-diisopropylethylamine complex, and the oxidation reaction and the reduction reaction are conducted in an aqueous buffer solution of about pH 7.5 to about pH 9.0 and at a temperature of about 15° C. to about 40° C.

Preferably, $X^+$ in formulas a, b and c represent $H^+$, $K^+$, $Na^+$ or $NH_4^+$. namely, the intermediate of formula c specifically is (R)-1,2,3,4-tetrahydroisoquinoline-1-carboxylic acid potassium salt, (R)-1,2,3,4-tetrahydroisoquinoline-1-carboxylic acid sodium salt, (R)-1,2,3,4-tetrahydroisoquinoline-1-carboxylic acid ammonium salt, or (R)-1,2,3,4-tetrahydroisoquinoline-1-carboxylic acid.

According to the present disclosure, the process for the synthesis of recombinant D-amino acid oxidase is: single colonies of recombinant *Escherichia coli* containing D-amino acid oxidase gene is inoculated to a LB liquid culture medium containing ampicillin, and activated at about 37±1° C. overnight for about 12 to about 16 hours. The activated culture is transferred to a liquid LB culture medium containing ampicillin, and shaking cultured at about 37±1° C. until OD600 value reaches about 0.6 to about 0.8, an inducer isopropyl-β-d-thiogalactopyranoside is then added to reach a final concentration of about 0.8 to about 1.0 mmol/L, and cultured at about 30±1° C. for about 8 to about 10 hours. The culture is centrifuged to collect precipitate which is added with a phosphate buffer of about pH 7 to about pH 9 to give a suspension. The suspension is ultrasonicated under ice bath and then centrifuged with the supernatant liquid from centrifugation being precooled to a temperature of about −20° C. to about −30° C. and freeze-dried for about 34 hours to about 40 hours to obtain powdery recombinant D-amino acid oxidase.

According to the present disclosure, preferred mole ratio of the compound of formula a or b and the borane-amine complex is about 1:1.1-5. The amounts of recombinant D-amino acid oxidase and catalase are preferred to be about 4% to about 6% (for example, 5%) and about 0.5% to about 1.5% (for example, 1%) of mass percent of the substrate in formula a or b, respectively.

Further, as to the oxidation reaction and the reduction reaction, preferred pH is about pH 8.0 to about pH 8.5, preferred temperature is about 20° C. to about 40° C.

Further, the aqueous buffer solution is preferably one or more selected from a group consisting of sodium phosphate, potassium phosphate and ammonia.

Preferably, a specific process for preparing the intermediate of formula c is as follow: compound in formula a or b is dissolved in a buffer solution, added with a borane-amine complex, led in oxygen or air, added with recombinant D-amino acid oxidase and catalase, then reaction is started under stirring and said temperature, which is monitored by HPLC, and ended when content of compound of formula a or formula b reduces to less than about 1 wt %.

Further, after ending the reaction, the system is heated at about 50° C. to about 60° C. to denature enzymes therein and filtered to remove enzymes (diatomite may be used to filter), the filtrate is added with acetone and filtered to collect precipitated crude solid which is recrystallized using a mixed solvent of water and acetone to give an intermediate of formula 1. Wherein, in the mixed solvent of water and acetone, the volume ratio of water and acetone is preferably about 1:1-3.

The present invention is further explained in detail by combining with specific embodiments in following, where it should be understood that the invention is not limited to the following examples. All substances used herein except recombinant D-amino acid oxidase can be purchased elsewhere commercially.

Example 1: Preparation of Recombinant D-Amino Acid Oxidase

Single colonies of recombinant *Escherichia coli* containing D-amino acid oxidase gene were inoculated from either a glycerol-containing tube or a transformation plate to a 4 mL LB liquid culture medium containing (100 μg/mL) ampicillin, and the mixture was activated at 37° C. overnight for 12-16 hours. The activated culture was then transferred to 100 mL liquid LB culture medium containing (100 μg/mL) ampicillin with an inoculum amount of 2%, and shaking cultured at 37° C. and at 200 rpm until $OD_{600}$ value reached about 0.6, when the inducer isopropyl-β-d-thiogalactopyranoside was added to reach a final concentration of 0.8 mmol/L, and further cultured overnight at 30° C. The culture was centrifuged (4° C., 5000 rpm, 15 min) to collect cells which were suspended with 10 mL of phosphate buffer (100 mM, pH 7.0). The cell suspension was ultrasonicated under ice bath for 10 minutes and centrifuged (4° C., 12000 rpm, 15 min). The supernatant liquid from centrifugation was precooled overnight at −20° C., and then freeze-dried for 34-40 hours to obtain the powdery recombinant D-amino acid oxidase.

Example 2: Preparation of Intermediate (R)-1,2,3,4-Tetrahydroisoquinoline-1-Carboxylic Acid Ammonium Salt 1.77 g (0.01 mol) DL-1,2,3,4-tetrahydroisoquinoline-1-carboxylic acid was dissolved in 5 mL ammonia (adjusting pH to 8.0), and 1.5 g (0.05 mol) borane-ammonia complex was added. Oxygen was inlet at a uniform speed, and 88.5 mg recombination D-amino acid oxidase and 18 mg catalase were respectively added. Under the condition of stirring, the reaction was conducted at 28° C. and monitored by HPLC. HPLC showed that after about 28 hours, (S)-1,2,3,4-tetrahydroisoquinoline-1-carboxylic acid ammonium salt was less than 1%. The reaction was ended, and the system was heated to 50-60° C. for more than half an hour to denature the enzyme proteins. The heated reactant was filtered by diatomite to remove the enzymes, the filtrate was diluted by adding two times volume of acetone and then filtered to collect precipitated crude product solid which was recrystallized with water/acetone (volume ratio 1/2) to give 1.8 g pure white solid, i.e. intermediate (R)-1,2,3,4-tetrahydroisoquinoline-1-carboxylic acid ammonium salt, with a separation yield of 92.5% and e.e. value of 99.3%.

The NMR data of the resulted product were as follow: $^1$H-NMR (400 MHz, $D_2O$, δ ppm): 3.07-3.10 (m, 2H, H-4), 3.45-3.66 (m, 2H, H-3), 4.95 (s, 1H, H-1), 7.29-7.54 (m, 4H, Ph), by which the product was confirmed to be (R)-tetrahydroisoquinoline-1-carboxylic acid ammonium salt.

Example 3: Preparation of Intermediate (R)-1,2,3,4-Tetrahydroisoquinoline-1-Carboxylic Acid Potassium Salt 1.77 g (0.01 mol) DL-1,2,3,4-tetrahydroisoquinoline-1-carboxylic acid was dissolved in 5 mL $K_2HPO_4$— $KH_2PO_4$ buffer solution (adjusting pH to 8.2), and 2.61 g (0.03 mol) borane-tert-butylamine complex was added. Oxygen was inlet at a uniform speed, and 35.5 mg recombination D-amino acid oxidase and 9 mg catalase were respectively added. Under the condition of stirring, the reaction was conducted at 35° C. and monitored by HPLC. HPLC showed that after about 30 hours, (S)-1,2,3,4-tetrahydroisoquinoline-1-carboxylic acid potassium salt was less than 1%. The reaction was ended and the solution was heated to 50-60° C. for more than half an hour to denature the enzyme proteins. The heated reactant was filtered by diatomite to remove the enzymes, the filtrate was extracted by toluene (3×5 mL) and the toluene phases were collected to recycle tert-butylamine (2.1 g). The extracted water phase was diluted by adding two times volume of acetone, and then filtered to collect precipitated crude product solid which was recrystallized with water/acetone (volume ratio 1/2) to give 1.98 g pure white solid, i.e. intermediate (R)-1,2,3,4-tetrahydroisoquinoline-1-carboxylic acid potassium salt, with a separation yield of 91.8% and e.e. value of 99.2%.

Example 4: Preparation of Intermediate (R)-1,2,3,4-Tetrahydroisoquinoline-1-Carboxylic Acid Sodium Salt 1.77 g (0.01 mol) DL-1,2,3,4-tetrahydroisoquinoline-1-carboxylic acid was dissolved in 5 mL $Na_2HPO_4$—$NaH_2PO_4$ buffer solution (adjusting pH to 8.0), and 1.77 g (0.03 mol) borane-dimethyl amine complex was added. Oxygen was inlet at a uniform speed, and 53.5 mg recombination D-amino acid oxidase and 9 mg catalase were respectively added. Under the condition of stirring, the reaction was conducted at 37° C., and monitored by HPLC. HPLC showed that after about 32 hours, (S)-1,2,3,4-tetrahydroisoquinoline-1-carboxylic acid sodium salt was less than 1%. The reaction was ended and the system was heated to 50-60° C. for more than half an hour to denature the enzyme proteins. The heated reactant was filtered by diatomite to remove the enzymes, the filtrate was diluted by adding two times volume of acetone and then filtered to collect precipitated crude product solid which was recrystallized with water/acetone (volume ratio 1/2) to give 1.86 g pure white solid, i.e. compound (R)-1,2,3,4-tetrahydroisoquinoline-1-carboxylic acid sodium salt, with a separation yield of 93.1% and e.e. value of 99.3%.

Example 5: Preparation of Intermediate (R)-1,2,3,4-Tetrahydroisoquinoline-1-Carboxylic Acid Ammonium Salt 1.77 g (0.01 mol) DL-1,2,3,4-tetrahydroisoquinoline-1-carboxylic acid was dissolved in 5 mL ammonia (adjusting pH to 8.5), and 3.45 g (0.03 mol) borane-triethylamine complex was added. Oxygen was inlet slowly, and 70.8 mg recombination D-amino acid oxidase and 12 mg catalase were respectively added. Under the condition of stirring, the reaction was conducted at 40° C., and monitored by HPLC. HPLC showed that after about 28 hours, (S)-1,2,3,4-tetrahydroisoquinoline-1-carboxylic acid ammonium salt was less than 1%. The reaction was ended, and the system was heated to 50-60° C. for more than half an hour to denature the enzyme proteins. The heated reactant was filtered by diatomite to remove the enzymes, the filtrate was diluted by adding two times volume of acetone and then filtered to collect precipitated crude product solid which was recrystallized with water/acetone (volume ratio 1/2) to give 1.81 g pure white solid, i.e. compound (R)-1,2,3,4-tetrahydroisoquinoline-1-carboxylic acid ammonium salt, with a separation yield of 93.3% and e.e. value of 99.3%.

Example 6: Preparation of Intermediate (R)-1,2,3,4-Tetrahydroisoquinoline-1-Carboxylic Acid Potassium Salt 1.77 g (0.01 mol) DL-1,2,3,4-tetrahydroisoquinoline-1-carboxylic acid was dissolved in 5 mL $K_2HPO_4$—$KH_2PO_4$ buffer solution (adjusting pH to 8.2), and 3.48 g (0.04 mol) borane-tert-butylamine complex was added. Oxygen was inlet at a uniform speed, and 47.5 mg recombination D-amino acid oxidase and 12 mg catalase were respectively added. Under the condition of stirring, the reaction was conducted at 35° C., and monitored by HPLC. HPLC showed that after about 35 hours, (S)-1,2,3,4-tetrahydroisoquinoline-1-carboxylic acid potassium salt was less than 1%. The reaction was ended, and the system was heated to 50-60° C. for more than half an hour to denature the enzyme proteins. The heated reactant was filtered by diatomite to remove the enzymes, the filtrate was diluted by adding two times volume of acetone and then filtered to collect precipitated crude product which was recrystallized with water/acetone (volume ratio 1/2) to give 1.99 g white solid, i.e. compound (R)-1,2,3,4-tetrahydroisoquinoline-1-carboxylic acid potassium salt, with a separation yield of 92.3% and e.e. value of 99.1%.

Example 7: Preparation of Intermediate (R)-1,2,3,4-Tetrahydroisoquinoline-1-Carboxylic Acid (R)-1,2,3,4-tetrahydroisoquinoline-1-carboxylic acid may be prepared using (R)-1,2,3,4-tetrahydroisoquinoline-1-carboxylic acid salts prepared in examples 1-6 respectively as stating material. A specific example is as follow:

1.99 g (R)-1,2,3,4-tetrahydroisoquinoline-1-carboxylic acid potassium salt prepared in example 6 was dissolved in 5 mL pure water, and hydrogen chloride gas was inlet into the solution until pH value reached 2-3.10 mL acetone was added and then the reaction mixture was filtered to collect precipitated solid which was dried to give 1.59 g (R)-1,2,3,4-tetrahydroisoquinoline-1-carboxylic acid, with e.e. value of 99.1% and a yield of 97%.

The NMR data of the resulted product was as follow:
$^1$H-NMR (DMSO-d6, 400 MHz, δ ppm): 2.87-3.11 (m, 2H, $CH_2CH_2N$), 3.35-3.76 (m, 2H, $CH_2CH_2N$), 5.3 (d, 1H, CHCOOH), 7.24-7.35 (m, 4H, ArH), 9.45 (s, 1H, COOH), by which the product was confirmed to be (R)-tetrahydroisoquinoline-1-carboxylic acid.

Example 8: Preparation of Intermediate (R)-1,2,3,4-Tetrahydroisoquinoline-1-Carboxylic Acid 1.77 g (0.01 mol) (S)-1,2,3,4-tetrahydroisoquinoline-1-carboxylic acid was dissolved in 5 mL $Na_2HPO_4$—$NaH_2PO_4$ buffer solution (adjusting pH to 8.5), and 5.72 g (0.04 mol) borane-N, N-diisopropylethylamine complex was added. Oxygen was inlet at a uniform speed, and 70.8 mg recombination D-amino acid oxidase and 12 mg catalase were respectively added. Under the condition of stirring, the reaction was conducted at 37° C. and monitored by HPLC. HPLC showed that after about 36 hours, (S)-1,2,3,4-tetrahydroisoquinoline-1-carboxylic acid sodium salt was less than 1%. The reaction was ended, and the system was heated to 50-60° C. for more than half an hour to denature the enzyme proteins. The heated reactant was filtered by diatomite to remove the enzymes, the filtrate was cooled down to 3-5° C., slowly dropwise added with concentrated hydrochloric acid to adjust pH to about 6.8, and a large amount of precipitates was precipitated and filtered to collect the precipitate. The filtrate after filtration was diluted by adding 2-3 times volume of acetone and then filtered to collect precipitate, and the precipitates were merged and recrystallized with water/acetone to give 1.66 g white solid, i.e. intermediate (R)-1,2,3,4-tetrahydroisoquinoline-1-carboxylic acid, with e.e. value of 99.3% and a separation yield of 93.5%.

Example 9: Preparation of Intermediate (R)-1,2,3,4-Tetrahydroisoquinoline-1-Carboxylic Acid 5.31 g (0.03 mol) (R, S)-1,2,3,4-tetrahydroisoquinoline-1-carboxylic acid was dissolved in 15 mL $K_2HPO_4$—$KH_2PO_4$ buffer solution (adjusting pH to 8.3), and 5.22 g (0.06 mol) borane-tert-butylamine complex was added. Air was inlet at a uniform speed, and 106.5 mg recombination D-amino acid oxidase and 27 mg catalase were respectively added. Under the condition of stirring, the reaction was conducted at 35 □ and monitored by HPLC. HPLC showed that after about 30 hours, (S)-1,2,3,4-tetrahydroisoquinoline-1-carboxylic acid potassium salt was less than 1%. The reaction was ended, and the solution was heated to 50-60° C. for more than half an hour to denature the enzyme proteins. The heated reactant was filtered by diatomite to remove the enzymes, the filtrate was extracted by toluene (3×10 mL) and the toluene phases were collected to recycle tert-butylamine (4.0 g). The aqueous phase after extracted was cooled down to 3-5° C., slowly dropwise added with concentrated hydrochloric acid to adjust pH to about 6.8, and a large amount of precipitates was precipitated and filtered to collect the precipitate. The filtrate after filtration was diluted by dropwise adding 2-3 times volume of acetone and then filtered to collect precipitate, and the precipitates were merged and recrystallized with water/acetone to give 5 g white solid, i.e. intermediate (R)-1,2,3,4-tetrahydroisoquinoline-1-carboxylic acid, with e.e. value of 99.3% and a separation yield of 93.7%.

Example 10: Preparation of (1R)-2-[(tert-butyl)oxycarbonyl]-1,2,3,4-tetrahydroisoquinoline-1-carboxylic acid (compound 1A)

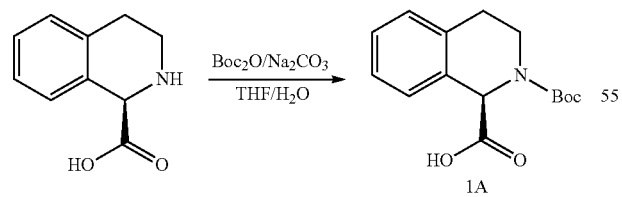

50 g (0.283 mol) (R)-1,2,3,4-tetrahydroisoquinoline-1-carboxylic acid was dissolved in 150 mL tetrahydrofuran and cooled down to 0-5° C., dropwise added with a solution of 120.2 g sodium carbonate (1.13 mol) dissolved in 450 mL water, and then a solution of 73.9 g $Boc_2O$ (0.339 mol) dissolved in 50 mL tetrahydrofuran was dropwise added into the reaction mixture, and the system was stirred overnight. After the end of reaction, the system was adjusted to be acidic and then extracted with ethyl acetate, and the extracted organic layers were merged, washed with saturated salt water, dried over anhydrous sodium sulfate, and vacuum-evaporated to remove the solvents. The dried residue was mashed with petroleum ether to give a white solid Boc-carboxylic acid, i.e. compound 1A.

Example 11: Preparation of (1R)-2-[(tert-butyl)oxycarbonyl]-1,2,3,4-tetrahydroisoquinoline formamide (compound 2A)

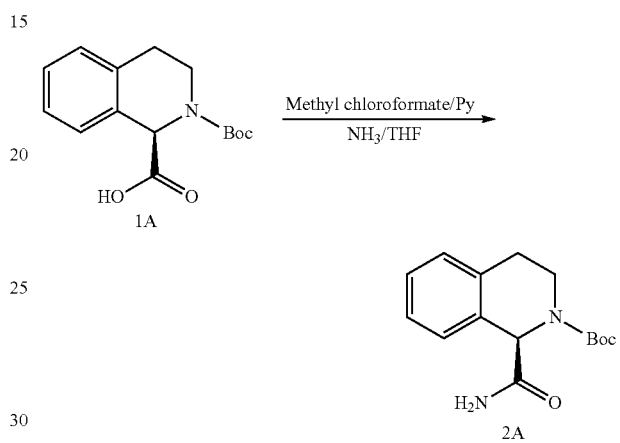

50 g compound 1A (180 mmol) was added into 200 mL tetrahydrofuran and cooled down to 0° C., added with 28.4 g pyridine (360 mmol), dropwise added with 23.4 g methyl chloroformate (216 mmol) and filtered to remove precipitates, the filtrate was further stirred for 1 hour, led in ammonia gas, and stirred overnight. The system was added with 10 mL water, extracted with 30 mL ethyl acetate for three times, and the extracted organic layers were dried over anhydrous sodium sulfate, filtered and concentrated. The residue was mashed with petroleum ether to give a white solid Boc-aminocarbonyl, i.e. compound 2A.

The NMR spectrum of the compound 2A is shown in FIG. 1, and NMR data was as follow: $^1H$ NMR (CDCl$_3$, 400 MHz, δ ppm): 1.47 (s, 9H, C(CH$_3$)$_3$), 2.70-2.92 (m, 2H, CH$_2$CH$_2$N), 3.68-3.76 (m, 2H, CH$_2$CH$_2$N), 5.31-5.60 (m, 1H, CH), 5.71-5.80 (m, 1H, CONH$_2$), 5.90-6.50 (m, 1H, CONH$_2$), 7.18-7.49 (m, 4H, ArH).

Example 12: Preparation of N—(((R)-1,2,3,4-tetrahydroisoquinoline-1-yl)methyl) cyclohexanecarboxamide hydrochloride (compound 4)

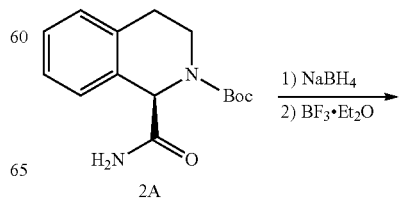

-continued

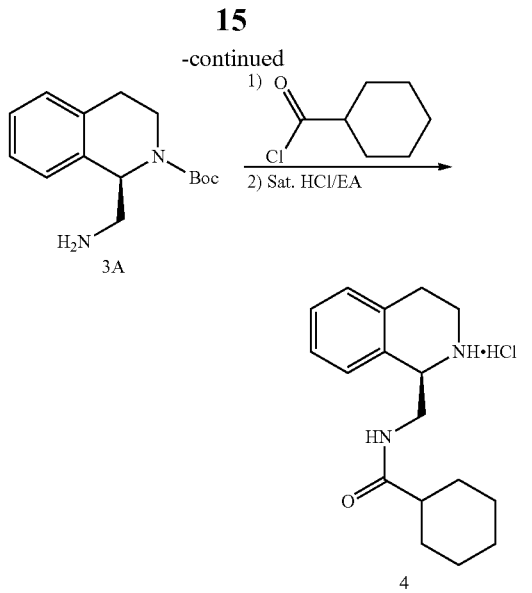

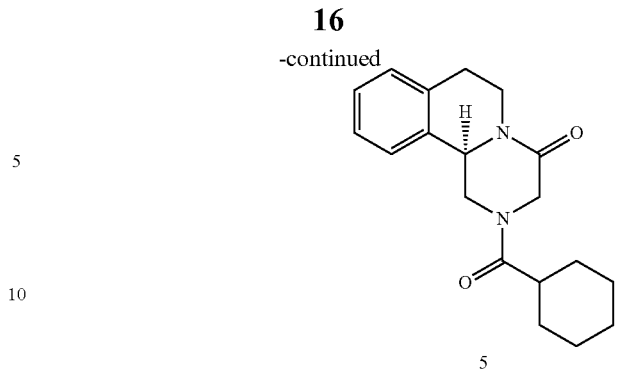

35 g compound 2A (126.7 mmol) was added into 350 mL tetrahydrofuran, batchwise added with 27 g sodium borohydride (633.5 mmol) at room temperature and under argon gas protection, heated to reflux, and dropwise added with 70 mL boron trifluoride diethyl etherate (633.5 mmol), then the generated suspension liquid was stirred for 2 hours. The starting material of amide was detected to disappear by TLC test when gas releasing was not obvious.

The reactant was poured into 0.1M HCl in ice water, adjusted to pH of 9 with 1N sodium hydroxide, and extracted with 50 mL dichloromethane for three times. The organic layers were washed with saturated salt water, dried over anhydrous sodium sulfate, filtered, and the solvent was removed to give 22 g crude product, i.e. compound 3A.

22 g crude compound 3A (83.86 mmol) was added into 230 mL acetonitrile, added with pyridine (125 mL, 125 mmol), cooled to 0-5° C., slowly dropwise added with a solution of 19.7 g cyclohexyl formyl chloride (135 mmol) dissolved in 71 mL dichloromethane, and after finishing addition, the mixture was stirred and reacted at room temperature overnight, vacuum-concentrated to remove the solvents to give 23.1 g residue.

The 23.1 g residue was dissolved in 200 mL saturated hydrogen chloride solution in ethyl acetate, stirred at room temperature overnight, rotationally evaporated to remove solvents, and the residue was recrystallized by methyl alcohol to precipitate a white solid which was vacuum-dried to give a cyclohexanol formamide hydrochloride, i.e. compound 4.

Example 13: Preparation of (R)-praziquantel, (1R)-2-(cyclohexanecarbonyl)-3,6,7,11b-tetrahydro-1H-pyrazino[2,1-a]isoquinolin-4-one (compound 5)

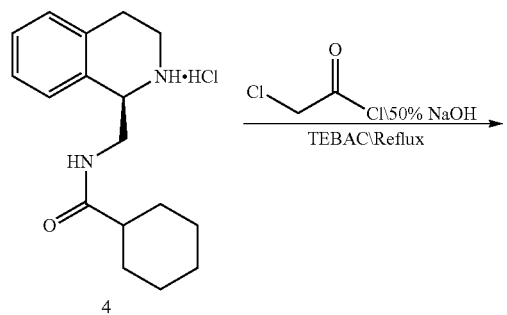

The white solid cyclohexanol formamide hydrochloride (22 g, 71.23 mmol) was dissolved into 90 mL dichloromethane, added with a solution of chloroacetyl chloride (8.29 g, 71.23 mmol) dissolved in 30 mL dichloromethane, and subsequently added with 50% NaOH solution (25.33 mL). After stirring for 30 min, benzyl triethyl ammonium chloride (TEBAC, 1.64 g, 7.12 mmol) was added, and the mixture was heated to reflux for 2 hours. After the end of reaction, 125 mL water was added, and the mixture was extracted with dichloromethane. The merged organic phases were respectively washed with water twice, with 5% hydrochloric acid solution and with saturated salt water, and dried over anhydrous sodium sulfate. After evaporating off the solvent, the residue was purified by silica gel column chromatography with PE/EA=20:1~5:1 as the eluent, and the targeted product were collected and concentrated. The concentrate was dissolved in ethyl acetate, heated to dissolve, slowly cooled down to precipitate crystals, filtered and dried to give a white solid, i.e. (R)-praziquantel, with e.e. value of 100% and a yield of 99.16%.

The NMR data of (R)-praziquantel was as follow: $^1$H NMR (300 MHz, DMSO-d6): δ 1.26-1.30 (m, 3H), 1.46-1.63 (m, 3H), 1.72-1.88 (m, 5H), 2.43-2.56 (m, 1H), 2.77-2.87 (m, 2H), 2.90-3.25 (m, 2H), 3.84-4.10 (m, 1H), 4.35-4.49 (m, 1H), 4.79-4.87 (m, 2H), 5.15-5.18 (d, 1H), 7.17-7.19 (d, 2H), 7.24-7.28 (d, 2H).

XRPD was used to test the white solid product, and the result showed that the product was a crystal, and had the same crystalline form according to the invention.

Example 14: Preparation of (1R)-2-[(tert-butyl)oxycarbonyl]-1,2,3,4-tetrahydroisoquinoline carboxylic amine (compound 3A)

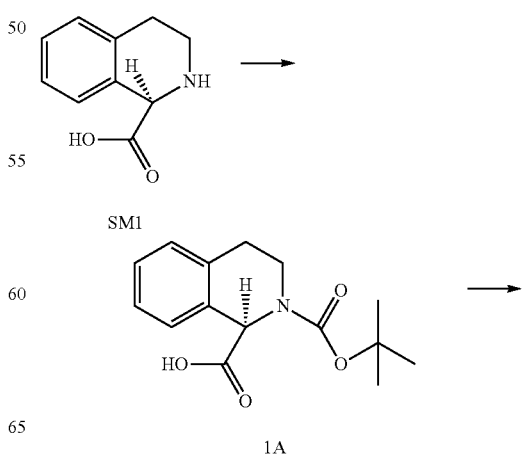

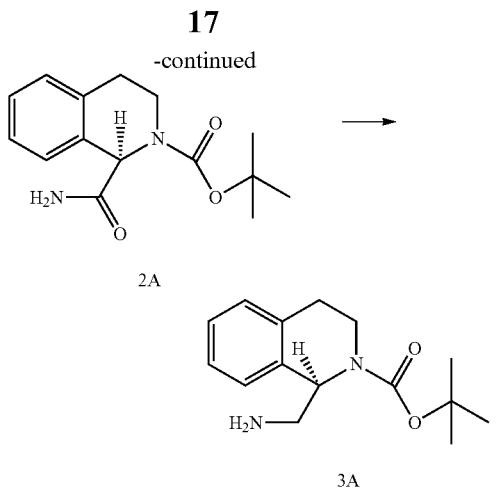

The preparation of compound 3A includes the following three steps:

(1) 2.27 g sodium hydroxide was dissolved into 67 mL water, added with 10 g (R)-1,2,3,4-tetrahydroisoquinoline-1-carboxylic acid (compound SM1), stirred for 30 minutes, then added with 67 mL ethyl alcohol, and 13.7 g Di-tert-butyl pyrocarbonate, dropwise added with 11.7 g triethylamine, and stirred at room temperature overnight. After reaction ended in the next day, the system was added with 68 mL water, rotationally evaporated to remove most of the solvent, adjusted by 1N HCl to pH 6-7 and filtered. The filter cake was washed with water to obtain a portion of compound 1A, and the filtrate was extracted with ethyl acetate and rotationally dried to obtain another portion of compound 1A. The product was dried to give 13.4 g crude with a yield of 86%, which was directly used in the next step.

(2) 13.4 g compound 1A was dissolved into 134 mL THF, added with 9.4 g CDI and stirred for 10 minutes, dropwise added with 67 mL ammonium hydroxide under ice bath, stirred for 15 minutes, added with 134 mL water after panels reaction ended, rotationally evaporated to remove most of THF, extracted with ethyl acetate to collect the organic phase. The organic phase was washed with salt solution, rotationally dried, concentrated to give the crude product, mixed and purified by column chromatography with DCM:MEOH=19:1 to give 10.53 g compound 2A with a yield of 80%.

(3) 7.4 g compound 2A (containing 10% dichloromethane) was dissolved into 74 mL tetrahydrofuran, added with 5.1 g sodium borohydride under nitrogen gas protect and ice bath, dropwise added with 21.5 mL $BF_3.Et_2O$ keeping the temperature below 10° C., and stirred for 42 hours at a temperature of 22-25° C. after the addition finished. After reaction ended, the system was cooled down to 0-5° C., and dropwise added with 10 mL water to quench the reaction, and then dropwise added with 375 mL 1N HCl in ice bath, heated to 10° C. and stirred for 1 hour, and the solution was detected to be alkaline. The system was extracted with 700 mL ethyl acetate, and then the aqueous layer was extracted with 200 mL ethyl acetate. The organic phases were merged and washed with 300 mL saturated sodium chloride solution for three times, rotationally dried, concentrated to give a crude product, mixed and purified by column chromatography with DCM:MeOH=19:1 (volume ratio) to give 6.2 g compound 3A (containing 10% dichloromethane) with a yield of 89%.

Above all, the present invention prepares (R)-praziquantel by combining biocatalytic approach with chemical synthesis method is more suitable for large-scale industrial production. By taking advantage of high stereoselectivity of recombinant D-amino acid oxidase, one enantiomer of racemate synthesized through chemical method is catalytically oxidated to imide intermediates and chemically reduced to racemate through in situ by a borane-amine complex, which realizes a method of continuously transforming the racemate into a single chiral isomer. The present invention employs a new enzymatic catalysis to reduce the amount of enzyme used. Compared with the prior art, the present invention overcomes the shortcomings of the traditional methods, and has advantages such as simple process for enzymatic catalysis, gentle, easily controllable for each of post-treatment steps, capable of utilizing existing manufacture infrastructure to reduce capital investment and the like, further reduces consumption of energy and organic solvents, and leads to an environmentally friendly green-chemistry production. It helps to address the unresolved industrial problem to synthesize (R)-praziquantel much more cost-effectively, and smooths the path to large scale manufacture of the active pharmaceutical ingredient.

The examples described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

The invention claimed is:

1. A process for the synthesis of (R)-praziquantel of formula 5:

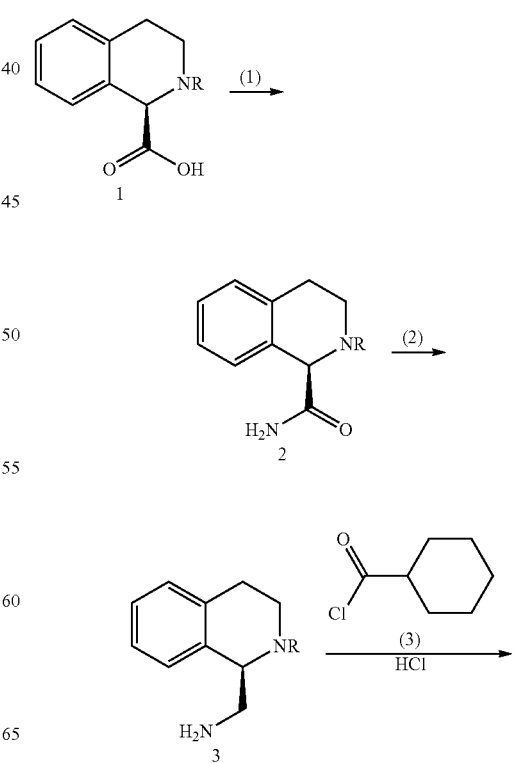

-continued

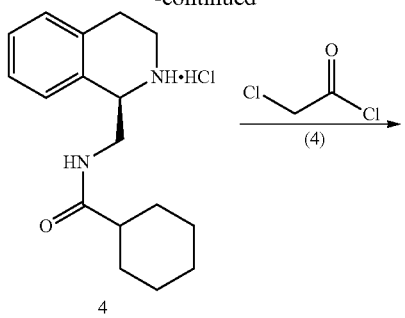

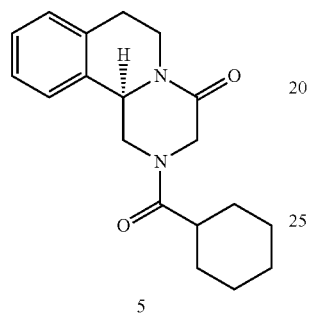

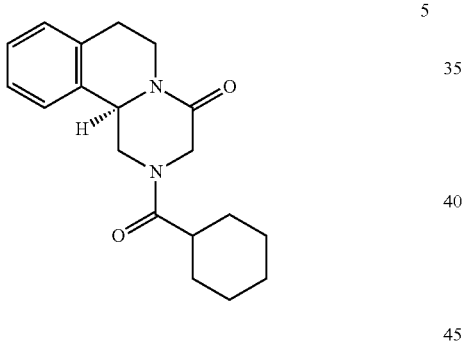

wherein the process comprises the following steps:
1) reacting a compound of formula 1:

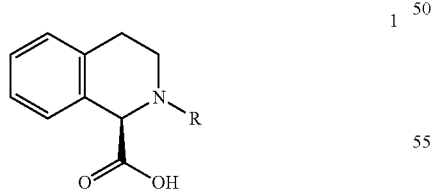

wherein R is selected from the group consisting of tert-butyloxycarbonyl, benzyloxycarbonyl, fluorenylmethoxycarbonyl, allyloxycarbonyl, trichloroethoxycarbonyl, p-methoxybenzyl and benzyl;
with (a) chloroformate in the presence of a base and solvent, followed by ammonia, or (b) N,N'-carbonyldiimidazole in the presence of solvent, followed by ammonia, to provide a compound of formula 2:

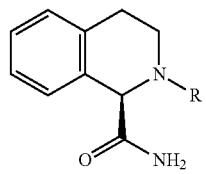

wherein R is selected from the group consisting of tert-butyloxycarbonyl, benzyloxycarbonyl, fluorenylmethoxycarbonyl, allyloxycarbonyl, trichloroethoxycarbonyl, p-methoxybenzyl and benzyl;
2) reacting the compound of formula 2 above with sodium borohydride in the presence of boron trifluoride diethyl etherate, to provide a compound of formula 3:

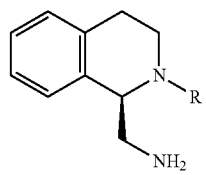

wherein R is selected from the group consisting of tert-butyloxycarbonyl, benzyloxycarbonyl, fluorenylmethoxycarbonyl, allyloxycarbonyl, trichloroethoxycarbonyl, p-methoxybenzyl and benzyl;
3) reacting the compound of formula 3 above with cyclohexanoyl chloride in the presence of a base and solvent, followed by hydrochloric acid to provide a compound of formula 4:

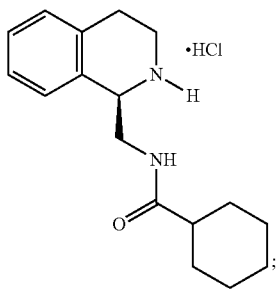

and 4) reacting the compound of formula 4 above with chloroacetyl chloride in the presence of a base and solvent, followed by benzyltriethylammonium chloride, to provide (R)-praziquantel of formula 5:

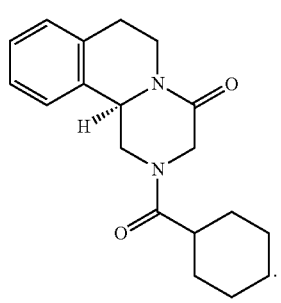

2. The process according to claim 1, wherein the base in (a) of step 1) is pyridine.

3. The process according to claim 2, wherein the pyridine is added at a temperature in the range of 0° C. to 5° C.

4. The process according to claim 1, wherein, in (b) of step 1), the compound of formula 1 is reacted with N,N'-carbonyldiimidazole in the presence of solvent to provide a compound of formula 2.

5. The process according to claim 4, wherein the N,N'-carbonyldiimidazole is added at ambient temperature.

6. The process according to claim 1, wherein, in step 2), the sodium borohydride is added at ambient temperature.

7. The process according to claim 6, wherein the boron trifluoride diethyl etherate is added dropwise.

8. The process according to claim 1, wherein, in step 2), the sodium borohydride and boron trifluoride diethyl etherate are added at a temperature below 10° C.

9. The process according to claim 1, wherein, in step 3), the base is pyridine.

10. The process according to claim 1, wherein, in step 4), the base is selected from the group consisting of sodium hydroxide, potassium hydroxide, potassium tert-butoxide and an organic amine, or a combination thereof.

11. The process according to claim 10, wherein the base is sodium hydroxide.

* * * * *